United States Patent [19]

Coburn et al.

[11] 4,287,191

[45] Sep. 1, 1981

[54] NOVEL SALICYLANILIDES AND MICROBIOCIDAL COMPOSITIONS AND USES THEREOF

[75] Inventors: Robert A. Coburn, Williamsville; Richard T. Evans, East Amherst; Robert J. Genco, Amherst, all of N.Y.; Armando Batista, Parque Lefevre, Panama

[73] Assignee: The Research Foundation of State University of New York, Albany, N.Y.

[21] Appl. No.: 140,098

[22] Filed: Apr. 14, 1980

[51] Int. Cl.³ .................... A01N 37/36; C07C 101/74; C07C 119/02
[52] U.S. Cl. .................... 424/230; 564/169; 564/177; 564/179
[58] Field of Search .............. 424/230; 564/169, 177, 564/179

[56] References Cited

U.S. PATENT DOCUMENTS

| | | | |
|---|---|---|---|
| 3,027,301 | 3/1962 | Freedman et al. | 424/230 |
| 3,113,067 | 12/1963 | Strufe et al. | 424/230 |
| 3,317,583 | 5/1967 | Hsi | 424/230 |
| 3,681,458 | 8/1972 | Ruschig et al. | 424/324 |
| 3,888,980 | 6/1975 | Meek | 424/230 |
| 3,917,617 | 11/1975 | Razdan et al. | 424/324 |
| 3,929,879 | 12/1975 | Taborsky | 424/559 S |
| 3,989,826 | 11/1976 | Forsyth et al. | 260/230 |
| 4,008,274 | 2/1977 | Sawatari et al. | 424/230 |
| 4,025,647 | 5/1977 | Eakin et al. | 424/226 |
| 4,200,632 | 4/1980 | Nakagawa et al. | 424/230 |

FOREIGN PATENT DOCUMENTS

| | | | |
|---|---|---|---|
| 1094578 | 3/1955 | France | 424/230 |
| 1299134 | 12/1962 | France | 424/230 |

OTHER PUBLICATIONS

Chem. Abst. 77, 14767(g) (1972) Rotmistrov et al.
Chem. Abst. 82, 97859(r) (1975) Umezawa et al.
Chem. Abst. 84, 58970(s) (1976) Umezawa et al.
Chem. Abst. 88, 69825(s) (1978) Stecker.

Primary Examiner—Douglas W. Robinson

[57] ABSTRACT

The composition comprises certain 5-acylsalicylanilides and more particularly comprises the compounds encompassed by the following generic formula:

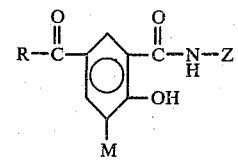

Where Z is a substituted phenyl ring of from 6 to 30 carbon atoms including substituents, R is a substituted or unsubstituted alkyl or phenyl group of from 2 to 30 carbon atoms including substituents and M is a radical selected from the group consisting of —C≡N,—F-,—NO$_2$,—H, lower alkyl or lower haloalkyl.

The preferred compositions of the invention have a partition coefficient greater than 4 and the substituted moieties in the phenyl ring of the Z group have a combined overall electron withdrawing effect on the phenyl ring of the Z group.

The method of the invention comprises contacting the microorganism with a sufficient concentration of the above composition for a sufficient time to inhibit the growth of the microorganism.

The above compositions are effective antiseptics against a wide range of microorganisms, especially bacteria, and the compositions surprisingly are especially effective against microorganisms prevalent in dental plaque.

37 Claims, No Drawings

NOVEL SALICYLANILIDES AND MICROBIOCIDAL COMPOSITIONS AND USES THEREOF

BACKGROUND OF THE INVENTION (a) Field Of The Invention

This invention relates to compositions and methods for killing or controlling the growth of microorganisms and more particularly relates to certain substituted salicylamide compositions having anti-microbial activity which are particularly useful in controlling the growth of microorganisms related to dental plaques and associated diseases.

(b) History Of The Prior Art

Historically compositions and methods have been sought for killing and controlling the growth of microorganisms, particularly those related to disease. The compositions which have been discovered for this purpose all have had one or more disadvantages. For example the compositions have not been effective against all undesireable microorganisms such as disease causing bacteria, have permitted certain microorganisms to develop an immunity or tolerance for the composition, have been more toxic than desireable, have caused allergic reactions in the host, or have been expensive and difficult to manufacture or purify.

These disadvantages have been particularly noticeable in compositions used to control the growth of bacteria related to dental plaques and associated diseases. Prior art compositions used for this purpose are either insufficiently effective, are too toxic or both. Toxic as used here in means that the composition causes damage to an organism, especially a human, which uses the composition to control the growth of an undesired microorganism whether the composition is applied topically or otherwise.

Many compositions formerly and even currently in use as oral antiseptics, and for that matter many antiseptics for other uses, contain large quantities of chlorine or bromine, often attached to a phenyl amine ring. In general such aromatic amine chlorinated and brominated compounds are to be avoided due to toxicity and sometimes carcinogenicity often associated with this type of compound. Furthermore such compounds which have low enough toxicity to be used as oral antiseptics are usually not sufficiently effective at low concentrations to treat dental plaques and associated diseases.

An example of a compound which contains chlorine attached to a phenyl amine ring which is or has been used as an oral antiseptic is chlorhexidine. Another compound which has been used is tribromosalan a brominated salicylanilide. This compound is effective but still is not as effective as desireable in killing or sufficiently inhibiting the growth of plaque causing organisms at concentrations as low as desired.

Compounds which are used as oral antiseptics which contain chlorine or bromine but not in a phenyl ring are cetylpyridinium chloride and domiphen bromide. These compounds are also insufficiently effective in controlling microorganisms associated with dental plaque, especially in dentrifrice compositions in which these compounds often become deactivated. Other antiseptics which contain chlorine attached to a phenyl ring but are not generally used in oral antiseptics are hexachlorophene and triclocarban. A non-halogenated oral antiseptic is hexylresorcinal. Hexylresorcinal is insufficiently effective against plaque forming organisms and in addition has a toxicity which is higher than desired. There are many other antiseptics but most have toxicities which are too high, especially for oral use.

Halogenated salicylanilides have been studied as possible antiseptic compounds; however most halogenated salicylanilides have now been banned by the United States Food and Drug Administration from certain over-the-counter products. This ban is due to adverse effects resulting from the use of such products. For example tetrachlorosalicylanilide has been shown to produce allergic reactions in man and certain other halogenated salicylanilides have been reported to produce photo-allergic reactions.

It has been reported that certain tertiary butyl substituted salicylanilides are bactericides against the bacterium Staphylococcus aureus. To the time of the present invention it is not known what additional microorganisms might be affected by this compound and there is no indication that it might be effective against the traditionally difficult bacteria involved in dental plaques and associated diseases. (Japanese patent No. 75,129,738 Oct. 14, 1975)

There is therefore a need for an effective non-toxic antiseptic for general purpose use which may be but is preferably not halogenated with chlorine or bromine and there is definitely a need for an non-toxic antiseptic which is effective against the microorganisms associated with dental plaques and associated diseases.

BRIEF DESCRIPTION OF THE INVENTION

In accordance with the present invention there is provided a novel composition which may be but is not necessarily halogenated with chlorine or bromine and which is an effective antiseptic with low toxicity in its preferred forms and which very surprisingly in its preferred forms is very effective against organisms associated with dental plaques, with forms of caries, with periodontal diseases and with other oral infections.

The compositions comprise certain 5-Acylsalicylanilides and more particularly comprise the compounds encompassed by the following generic formula:

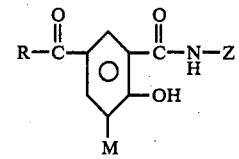

Where Z is a substituted phenyl ring of from 6 to 30 carbon atoms including substituents, R is a substituted or unsubstituted alkyl or phenyl group of from 2 to 30 carbon atoms including substituents and M is a radical selected from the group consisting of $-C\equiv N$, $-F$, $-NO_2$, $-H$ lower alkyl or lower haloalkyl.

The preferred compositions of the invention have a partition coefficient greater than 4 and the substituted moieties in the phenyl ring of the Z group have a combined overall electron withdrawing effect on the phenyl ring of the Z group.

The above compositions are effective antiseptics against a wide range of bacteria and the preferred compositions surprisingly are especially effective against a prevalent microorganism in dental plaque, Actinomyces viscosus, and in addition are effective against many other organisms associated with periodontal diseases including *Actinomyces naeslundii, Streptococcus mutans, Bacteroides melaninogenicus asaccharolyticus, Bacteroides melaninogenicus intermedius,* and *Streptoccus sanguis.*

DETAILED DESCRIPTION OF THE INVENTION

As previously mentioned, the present invention is concerned with certain antiseptic compositions and particularly certain 5 acyl derivitives of salicylanilides. These compositions all have at least some antiseptic properties and the preferred compositions have excellent antiseptic properties especially against microorganisms associated with dental plaques and associated oral diseases. Furthermore many of these compositions are characterized by having low toxicity to mammals. Additionally the invention includes the method for controlling the growth of microorganisms by contacting the microoganisms with a composition of the invention for a sufficient time to kill or inhibit the growth or reproduction of the organism. The contact of the microorganism with the composition may be accomplished in either in vivo or in vitro environments. The compositions comprise certain 5-Acylsalicylanilides and more particularly comprise the compounds encompassed by the following generic formula:

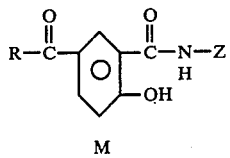

M

Where Z is a substituted phenyl ring of from 6 to 30 carbon atoms including substituents, R is a substituted or unsubstituted alkyl or phenyl group of from 2 to 30 carbon atoms including substituents and M is a radical selected from the group consisting of —C≡N,—F-,—NO₂,—H lower alkyl or lower haloalkyl.

The preferred compositions of the invention have a partition coefficient greater than 4 and the substituted moieties in the phenyl ring of the Z group have a combined overall electron withdrawing effect on the phenyl ring of the Z group.

Partition coefficient of a composition as used herein is the $log_{10}$ P where P is the ratio of the concentration of the composition in octanol to the concentration of the composition in water in a two phase octanol-water system. A partition coefficient of 4 therefore means that the ratio of the concentration of the composition in octanol to the concentration in water is $10^4$ or 10,000 to 1. The partition coefficient is a measure of the lipophylic character of the compound. The preferred compositions of the invention are lipophylic as indicated by a partition coefficient of greater than 4. The partition coefficient is however usually less than 10.

"Substituted" as used herein means that the organic composition or radical to which the term is applied is:
(a) made unsaturated by the elimination of elements or radical; or
(b) at least one hydrogen in the compound or radical is replaced with a moiety (Y) containing one or more carbon, oxygen, sulfur, nitrogen or halogen atoms; or
(c) both a) and b).

Moieties which may replace hydrogen, as previously described, which contain only carbon and hydrogen are all hydrocarbon moieties including alkyl, alkenyl, alkynyl, alkyldienyl, cycloalkyl, phenyl, alkylphenyl, naphthyl, anthryl, phenanthryl, fluoryl, steroid groups, and combinations of these groups with each other and with polyvalent hydrocarbon groups such as alkylene, alkylidene and alkylidyne groups. Specific examples of such groups are:

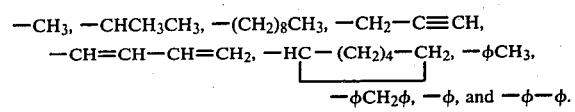

Moieties containing oxygen which may replace hydrogen as previously described include hydroxy, acyl or keto, ether, epoxy, carboxy, and ester containing groups. Specific examples of such oxygen containing groups are:

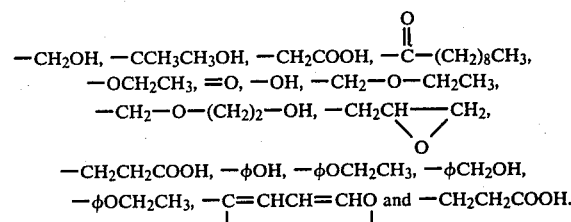

Examples of moieties containing sulfur are the sulfur containing acids and acid ester groups, thioether groups, mercapto groups and thioketo groups. Specific examples of such groups are:

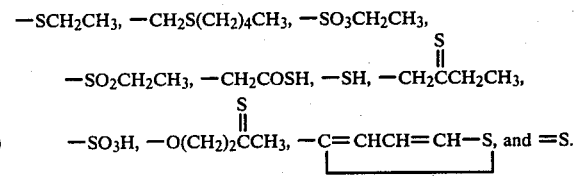

Examples of moieties containing nitrogen are amino groups, the nitro group, azo groups, ammonium groups, amide groups, azido groups, isocyanate groups, cyano groups and nitrile groups. Specific examples of such groups are:

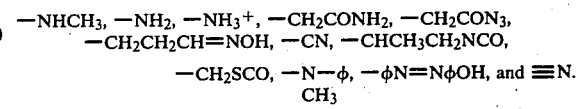

Examples of moieties containing halogen are chloro, bromo, fluoro, iodo groups and any of the moieties previously described where a hydrogen or a pendant alkyl group is substituted by a halo group to form a stable substituted moiety.

Specific examples of halogen containing moieties are: —(CH₂)₃COCl, —φF₅, —φCl, —CF₃, and —CH₂φBr.

It is understood that any of the above moieties can be substituted into each other in either a monovalent substitution or by loss of hydrogen in a polyvalent substitution to form another monovalent moiety which can replace hydrogen in the organic compound or radical. "Lower alkyl" as used herein means an alkyl group of from 1 through 5 carbon atoms. "—φ" as used herein represents a phenyl ring.

A generic formula which includes many of the preferred compositions of the invention is:

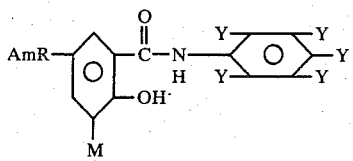

R is

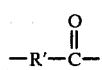

where —R'— is a saturated or unsaturated halogenated or unhalogenated alkylene or phenylene group containing 2 through 20 carbon atoms. —R'— may be cycloalkylene, e.g. cyclohexylene. Examples of preferred —R'— groups are: —φ—, —(CH$_2$)$_6$—, —(CH$_2$)$_8$—, and —(CH$_2$)$_{10}$—. Other —R'— groups are —(CH$_2$)$_6$(CCl$_2$)—, —(CF$_2$)$_6$—, and —(CCl$_2$)$_8$—. It is apparent that the forgoing are only examples of possible —R'— groups.

A is independently at each occurrence —H, —OH, —halogen, lower alkoxy, lower alkyl, —SH, thioalkyl, phenyl, phenoxy, —NH$_2$, lower amino or lower acyl group. A is most preferably methyl (—CH$_3$) or —H. In general when A contains oxygen or another group or element which tends to increase the hydrophylic nature of the R group, additional lipophylic groups or elements must be present so that the overall hydrophylic-lipophylic balance of the R group decidedly favors solubility in fats or oils. As used herein lipophylic means the tendency to be attracted to fats or oils and as is well known hydrophylic means to be attracted to water. The R group should in fact be sufficiently lipophylic to give an overall lipophylic character to the composition, i.e. a partition coefficient greater than 4.

m is an integer of from 1 through 3 and in the preferred embodiments of the invention is usually 1 since pendant groups from the —R'— moiety usually do not add greatly to the antimicrobial character of the compounds and even if they do the same pendant groups often can increase toxicity to mammals. Pendant groups which are hydrophylic in particular have been found to reduce anti-microbial activity unless more lipophylic groups are added to the R moiety to offset them.

Y is independently at each occurrence —H, lower alkyl, halogenated lower alkyl, —NO$_2$, —CN, —halogen, lower acyl, —SO$_2$R″, or —SO$_3$R″ where R″ is lower alkyl or halogenated lower alkyl, provided that at least one of Y is not H or lower alkyl. Generally Y is not chlorine or bromine when applied to humans due to the increased toxicity or carcinogenicity often associated with halogenated phenyl rings. Halogen has however been found to sometimes even further increase antimicrobial activity and thus is nevertheless sometimes used especially when the compound is used only in in-vitro environments. Halogen, especially fluorine, can be used with benefit and very little or no increase in toxicity when the halogen is attached to an aliphatic carbon atom instead of directly to the phenyl ring. An example of a very good Y group is —CF$_3$. In general all good Y groups are electron withdrawing groups and desireably are not strongly hydrophylic or water solubilizing groups. A particularly good Y group is —NO$_2$ especially when it is in the 4' position on the phenyl ring. Another very good Y group is —F especially when located in all of the Y positions on the phenyl ring. M is as previously described.

Examples of compounds especially suitable for use in accordance with the invention are those compounds wherein A is —H, m=1, Y is —NO$_2$, —Br or —Cl in the 4' position or —CF$_3$ in the 3', 4' or 5' position or —F in all Y positions. Examples of other compounds highly suitable for use in accordance with the invention are those compounds wherein m is 1 or 2, at least one A is not —H and Y is independently at each occurrence —H, —halogen, —NO$_2$, —CN, halogenated lower alkyl, —CHO, or lower acyl. R' may be cycloalkylene as previously discussed.

Examples of specific compounds in accordance with the invention are the compounds having the formula:

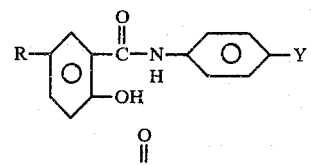

where R is CH$_3$(CH$_2$)$_8$C(O)— and Y is —NO$_2$;

where R is CH$_3$(CH$_2$)$_{10}$C(O)— and Y is —NO$_2$;

where R is CH$_3$(CH$_2$)$_6$C(O)— and Y is —NO$_2$;

where R is CH$_3$(CH$_2$)$_{10}$C(O)— and Y is —Br; and where R is CH$_3$(CH$_2$)$_8$C(O)— and Y is —Br.

where R is CH$_3$(CH$_2$)$_8$C(O)— and Y is —CF$_3$ where R is CH$_3$(CH$_2$)$_{10}$C(O)— and Y is —CF$_3$ where R is CH$_3$(CH$_2$)$_6$C(O)— and Y is —CF$_3$ More examples of preferred compounds in accordance with the invention are those compounds having the formula:

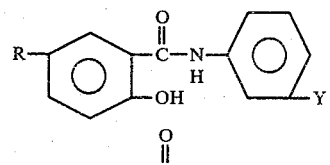

where R is CH$_3$(CH$_2$)$_8$C(O)— and Y is —CF$_3$; and where R is CH$_3$(CH$_2$)$_{10}$C(O)— and Y is —CF$_3$;

Additional examples of preferred compounds are those compounds having the formula:

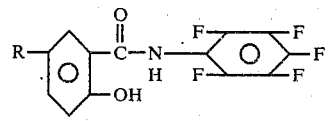

-continued

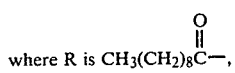
where R is CH$_3$(CH$_2$)$_8$C—,

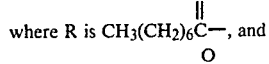
where R is CH$_3$(CH$_2$)$_6$C—, and

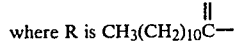
where R is CH$_3$(CH$_2$)$_{10}$C—

An even further example is the composition of the formula:

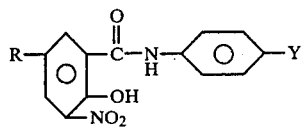

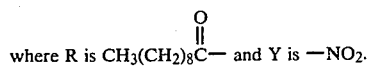
where R is CH$_3$(CH$_2$)$_8$C— and Y is —NO$_2$.

The method in accordance with the present invention for inhibiting the growth of microorganisms and especially bacterial organisms comprises contacting the organism for a sufficient time with a sufficient concentration of the composition of the invention, suitable compositions being those previously generically and specifically described. In general the sufficient concentration of the composition is from about 0.1 to about 5 micrograms per milliliter of medium containing the organism. For very difficult microorganisms, e.g. fusobacteria, the concentration required may be substantially higher, e.g. as much as 50 micrograms per milliliter. The medium may be any solid or liquid. Examples of media within or upon which the composition may be used are organic tissue, dental surfaces, floors, walls, hardware and implements in general, paints, textiles, leather, synthetic resins and in the future perhaps foods and medicines and other ingestible substances. The compositions may be used in or on the media as antiseptics, disinfectants, antimicrobial medicines or preservatives. It is to be understood that the above sufficient concentrations are those required to be in actual contact with the microorganism and substantially higher concentrations may be required in antiseptic preparations when penetration through a substance is required in order to contact the microorganism with the composition of the invention. The sufficient time is the time required to inhibit the growth of the microorganism and may be the entire time of inhibition and when the microorganism is killed by the composition is usually from about 10 seconds to 30 minutes.

The compositions may be used as additives to soaps, deodorants and sterilizing solutions to enhance or provide antimicrobial properties to these products.

Microorganism as used herein includes any microorganism whose growth can be inhibited by the compositions of the invention. Such microorganisms include almost all bacteria and are also believed to include many fungi. It is also possible that some other protists and perhaps even some viruses are included.

In general the compositions in accordance with the invention are prepared by reacting a lower alkyl salicylate with an acyl chloride to form a 5-acylsalicylic acid after saponification. The 5-acylsalicylic acid is then reacted with a substituted aniline to form the 5-acylsalicylanilide. More specifically the synthesis of the compositions in accordance with the invention is believed to follow the following reaction path:

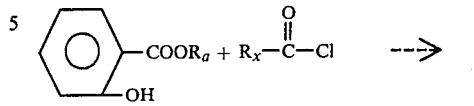

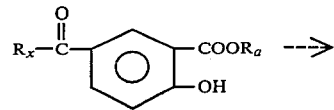

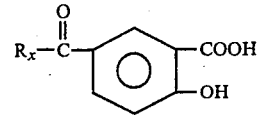

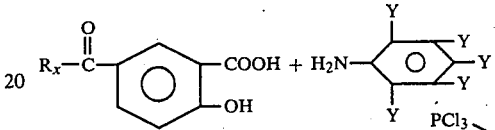

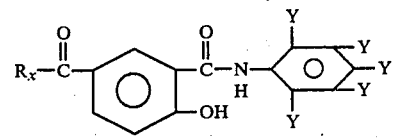

$R_a$ is lower alkyl and is usually methyl. Lower alkyl as used throughout this specification means alkyl of from 1 through 4 carbon atoms. $R_x$— is AmR'—. AmR' and Y are as previously described. An M group may be present in the original ester reactant.

As a usual procedure, a reaction solvent is used to form the 5-acylsalicylic acid. A preferred reaction solvent is carbon disulfide. Anhydrous aluminum chloride or other Lewis acid is added to the carbon disulfide and the mixture is cooled, e.g. with ice. A solution of the alkyl salicylate, e.g. methyl salicylate, and acyl chloride in carbon disulfide or other reaction solvent is then slowly added and the temperature is maintained below about 10 degrees C. After complete reaction which may take as long as 24 hours, the reaction mass is poured into ice water and the mixture is then extracted with a suitable solvent such as ether, washed, dried over anhydrous sodium sulfate and evaporated in a vacuum. The residue is dissolved in a suitable solvent such as ethanol and treated with a solution of an alkali metal hydroxide, e.g. 2 N NaOH solution. After heating to a temperature of between about 80 and 120 degrees C., e.g. on a steam bath, the mass is cooled and acidified with a suitable acid such as HCl to pH of about 1 to precipitate the product. Recrystallization from ethanol gives purified 5-acylsalicylic acid.

5-acylsalicylic acid is reacted with the appropriate substituted aniline, e.g. p-nitro aniline, in a suitable reaction solvent such as chlorobenzene. Desireably the 5-acylsalicylic acid is pre-reacted with phosphorous trichloride in the solvent at a suitable temperature, e.g. between about 55 and 80 degrees C. The reaction time is usually between about one and about five hours. The solution is then cooled and the appropriate substituted aniline, e.g. nitroaniline is then added and the solution is again heated to the suitable temperature, e.g. between 55 and 80 degrees as previously described for from about one to five hours and then is refluxed until the reaction is complete, e.g. for 24 hours. The solvent is then removed in a vacuum and the residue is purified by recrystallization from a mixture of a suitable solvent such as a mixture of ethanol and water. The resulting product is the 5-acylsalicylic acid of the invention The following examples serve to illustrate and not limit the present invention.

EXAMPLE 1

Preparation of 5-n-decanoylsalicylic acid

A one-liter three-neck flask is fitted with a 250 ml dropping funnel, a mechanical overhead stirrer, and a condenser with a drying tube. A mixture of anhydrous aluminum chloride (120 g., 0.9 moles) and carbon disulfide (250 ml) is placed in the flask and cooled to 0-5 degrees C. with an ice bath. A solution of methylsalicylate (45.6 g., 0.3 mole) and n-decanoyl chloride (115.4 g., 0.6 mole) in carbon disulfide (50 ml) is then added through the dropping funnel over the course of three hours while maintaining the temperature of the reaction mixture below 10 degrees C. The reaction mixture is then allowed to warm to room temperature and stirring is continued for 24 hours. The mixture is then poured slowly onto cracked ice (500 g.) and the resulting slurry is stirred until the ice melts. The slurry is then extracted with four 50 ml portions of diethyl ether and the combined ether extracts are washed with water and dried over anhydrous sodium sulfate. Any remaining liquid is removed by evaporation in a vacuum. The residue is dissolved in ethanol (50 ml) and added to 200 ml of 2 N sodium hydroxide solution which is then heated on a steam bath for 12 hours. The solution is then cooled and acidified with concentrated hydrochloric acid to pH 1 which results in a precipitate which is collected in a Büchner funnel. Recrystallization from ethanol-water gives 165 g. of 5-n-decanoylsalicylic acid, mp 118°-119° C.

EXAMPLE 2

Preparation of 5-n-decanoyl-4'nitrosalicylanilide abreviated AN-10.

In a 100 ml round-bottom flask fitted with a condenser and drying tube is placed 5-n-decanoylsalicylic acid (1.85 g., 6.7 mmoles), dry chlorobenzene (50 ml), and phosphorous trichloride (0.47 g., 3.4 mmoles). The mixture is then stirred by means of a magnetic stirring bar while the mixture is heated to 60° C. for three hours. The resulting solution is cooled to room temperature and 0.93 g. (6.7 mmoles) of p-nitroaniline is added. The mixture is then heated to 60° C. for three hours, with stirring, and then refluxed for 24 hours. The solvent is removed by vacuum vaporization and the residue is recrystallized from ethanol-water. The crystalline product is triturated with concentrated hydrochloric acid, collected and washed with water. Recrystallization from ethanol-water gives 0.64 grams of 5-n-decanoyl-4'-nitrosalicylanilide, mp 142°-143° C.

EXAMPLE 3

Acute oral toxicity of AN-10

Sixteen female white rats averaging 265 grams in weight were fasted overnight and divided into four groups of four animals each. In one group each animal received, by gavage tube, 4 ml of an aqueous solution of 1% methylcellulose, the drug delivery vehicle. This group was the control group. The remaining three groups received doses of 50, 750, and 2000 mg/kg of AN-10 in 4-ml aqueous suspension, respectively.

Within the first week following this single dose only one animal died. This animal had received the 50 mg/kg dose. Examination of the animal showed a punctured trachea thus this death can be attributed to trauma associated with administration.

From this experiment it can be concluded that the $LD_{50}$ for AN-10 by the single dose oral route is greater than 2000 mg/kg in Osborne-Mendel white rats.

EXAMPLE 4

Plaque growth inhibition

The composition prepared in example 2 above is tested in vitro for plaque inhibition in comparison with prior art compounds. The test used is set forth in detail in *Comparison of Antiplaque Agents Using an In Vitro Assay Reflecting Oral Conditions* by R. T. Evans et al, Journal of Dental Research, June 1977.

In summary bovine mandibles, obtained immediately after slaughter, are cut into 4×8 mm slabs and sterilized in a 0.15 M NaCl solution buffered at a pH of 7.5 with 0.02 M sodium phosphate (PBS soln.) Before use the slabs are coated with sterile saliva and then rinsed twice in sterile PBS. The slabs are then placed in small plastic petri dishes containing various concentrations of the compositions to be tested. The test solution used in accordance is a solution of the composition in a mixture of 20% by volume of ethanol, 40% by volume of propylene glycol and 40% by volume of a pH 8 aqueous buffer solution containing mono and di sodium phosphates. The slabs are left in the solution of the composition for two minutes and then rinsed in sterile PBS solution. After rinsing, each slab is placed in a 10×75 mm cotton stoppered glass culture tube containing 1 ml of sucrose-broth culture medium which is then innoculated with a 24 hour culture of the desired microorganism standardized to an optical density $(OD)_{540}$ of 1.0 for *A. naeslundii* and *S. sanguis* and of 0.75 for *A. viscosus* and *S. mutans*. 50 μl of the inoculation medium is used. *A. viscosus* is incubated under aerobic conditions and the others are incubated under anaerobic conditions (5% $CO_2$ and 95% $H_2$). After incubation for about 24 hours the nonadherent organisms are removed and the tube is rinsed twice with 0.5 ml of PBS and the washings combined with the nonadherent organisms.

The tooth slabs are then transferred to 1 ml of 0.1 N NaOH and 1 ml of 0.1 N NaOH is also added to the glass culture tubes. The slabs and tubes are then sonically agitated, if necessary to suspend the adherent organisms. The optical density of each of the three fractions is then measured on a spectophotometer. The tests are repeated with varying concentrations of the compositions being tested until growth inhibition curves can be developed. The 50% growth inhibition dosages $(ID_{50})$ are then determined with a reliability of + or −80% or better. The results are set forth in Table 1.

TABLE 1

| Compound Tested | Microorganism Tested | $ID_{50}$ Total Growth | $ID_{50}$ Adherent Growth | % Inhibition @ Mol.Conc. |
|---|---|---|---|---|
| AN-10 | A. viscosus | $7.3 \times 10^{-5}$ | $7.0 \times 10^{-5}$ | 96% @ $1 \times 10^{-4}$ |
| AN-10 | A. naeslundii | $8.3 \times 10^{-5}$ | $4.3 \times 10^{-5}$ | 96% @ $3.3 \times 10^{-4}$ |

TABLE 1-continued

| Compound Tested | Microorganism Tested | ID$_{50}$ Total Growth | ID$_{50}$ Adherent Growth | % Inhibition @ Mol.Conc. |
|---|---|---|---|---|
| AN-10 | S.sanguis | $3.7 \times 10^{-4}$ | $6.7 \times 10^{-4}$ | 86% @ $1 \times 10^{-3}$ |
| AN-10 | S.mutans | $1.6 \times 10^{-3}$ | $2.3 \times 10^{-2}$ | 59% @ $1 \times 10^{-3}$ |
| Tribromosalan (TBS) | A.viscosus | $8.8 \times 10^{-4}$ | $2.3 \times 10^{-4}$ | 53% @ $1 \times 10^{-3}$ |
| TBS | A.naeslundii | $4.0 \times 10^{-4}$ | $3.2 \times 10^{-4}$ | 86% @ $1.5 \times 10^{-3}$ |
| TBS | S.sanguis | $5.1 \times 10^{-4}$ | $1.3 \times 10^{-2}$ | 46% @ $1 \times 10^{-3}$ |
| TBS | S.mutans | $1.4 \times 10^{-3}$ | $4.7 \times 10^{-4}$ | 46% @ $1.5 \times 10^{-3}$ |
| Chlorhexidine (CLHX) | A.viscosus | $2.3 \times 10^{-5}$ | $2.9 \times 10^{-5}$ | 85% @ $1 \times 10^{-3}$ |
| CLHX | A.naeslundii | $4.4 \times 10^{-3}$ | $5.1 \times 10^{-3}$ | 78% @ $1 \times 10^{-3}$ |
| CLHX | S.sanguis | $3.9 \times 10^{-4}$ | $8.5 \times 10^{-2}$ | 70% @ $1 \times 10^{-3}$ |
| CLHX | S.mutans | $8.6 \times 10^{-5}$ | $9.7 \times 10^{-5}$ | 95% @ $1 \times 10^{-3}$ |
| Fluorophene (SBF-1) | A.viscosus | $5.9 \times 10^{-5}$ | $6.7 \times 10^{-4}$ | 65% @ $3.3 \times 10^{-3}$ |
| SBF-1 | S.mutans | $1.8 \times 10^{-3}$ | $1.5 \times 10^{-3}$ | 86% @ $2 \times 10^{-3}$ |

As can be seen from the foregoing table, AN-10, a compound of the present invention, is as good as or better than the commercial compounds tested in overall inhibition of the growth of the microorganisms tested. The organisms tested are believed to represent the most prevalent microorganisms associated with dental plaque. The only compound tested which is even comparable to AN-10 in overall effectiveness is chlorhexidine which, as previously discussed, is not desirable since it is a chlorinated aromatic amine. This test clearly shows the strong substantivity of AN-10 to a substrate to inhibit growth of microorganisms.

EXAMPLE 5

Bactericidal effects against established dental plaque

In vitro plaques are grown on no. 20 nichrome wires by fixing the wires to culture tube closures to suspend the wires into a complex culture medium supplemented with 5% by wt of sucrose and 0.005% sodium carbonate. Separate cultures are initially inoculated with A. viscosus and S. mutans and the wires are transferred daily to fresh medium until the wire-adherent microorganisms form well established plaques. All cultures are incubated at 37 degrees C. Plaque coated wires are then immersed in a solution of composition to be tested. The compositions tested are AN-10 and Chlorhexidine. The immersion time is two minutes. The solution in which the composition is dissolved is the same solution used to dissolve the composition in the previous example. The plaque is then rinsed with distilled water and transferred to fresh medium. The lack of growth in the fresh medium is considered as an indication that the microorganisms have been killed. Further plaque coated wires are treated as previously described until sufficient information is obtained to determine the minimum concentration of composition required to kill the microorganisms. The results are set forth in Table 2.

TABLE 2

| Microorganism | Minimum Concentration Required for Complete Bactericidal Effect | | |
|---|---|---|---|
| | AN-10 | Chlorhexidine | TBS |
| A.viscosus | 125 µg/ml | 500 µg/ml | 500 µg/ml |
| S.mutans | 62.5 µg/ml | 250 µg/ml | 1000 µg/ml |

An examination of Table 2. clearly shows that AN-10 is far superior to chlorhexidine in killing the microoganisms tested in established dental plaque with a short contact time.

EXAMPLE 6.

Effectiveness of Other Compositions of the Invention

Several other compositions of the invention manufactured in essentially in accordance with the general process previously described are tested for antimicrobial activity against Actinomyces viscosus(A. viscosus) by introducing various concentrations of the compound to be tested into growth medium inoculated with the microorganism to determine the minimum concentration which will completely inhibit growth. The results are set forth in Table 3.

TABLE 3

| Composition Tested | Min. Conc. |
|---|---|
| 5-n-dodecoyl-3'-trifluoromethylsaliclyanilide | 0.5–1.0 µg/ml |
| 5-n-dodecoyl-4'-nitrosalicylanilide | 0.05 µg/ml |
| 5-n-octoyl-4'-nitrosalicylanilide | 0.125 µg/ml |
| 5-n-decoyl-4'-bromosalicylanilide | 0.125 µg/ml |
| 5-n-dodecoyl-4'-bromosalicylanilide | 0.05 µg/ml |

EXAMPLE 7

AN-10 is tested for effectiveness against the bacterium Staphylococcus aureus in accordance with the procedure set forth in Example 6. The minimum concentration to completely inhibit growth of the microorganism is found to be less than 10 micrograms per milliliter. This example, in conjunction with the previous example clearly demonstrates the broad spectrum effect of this compound of the invention.

EXAMPLE 8

5-n-octanoyl-2',3',4',5',6'pentafluorosalicylanilide is tested for effectiveness against S. mutans essentially in accordance with the procedure of Example 6. The minimum concentration which will completely inhibit growth of this microorganism is found to be about 0.5 micrograms per milliliter.

What is claimed is:

1. A compound having the formula:

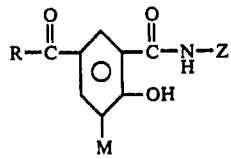

where Z is substituted phenyl ring of from 6 to 30 carbon atoms including substituents, R is a substituted or unsubstituted alkyl or phenyl group of from 2 to 30 carbon atoms including substituents and M is a radical selected from the group consisting of —C≡N, —F, —NO₂, —H, lower alkyl and lower haloalkyl, said composition having a partition coefficient greater than 4 and the substituted moieties in the phenyl ring of the Z group having a combined overall electron withdrawing effect on the phenyl ring of the Z group.

2. An antiseptic composition comprising an antimicrobial effective amount of a compound of claim 1 and a suitable carrier therefor.

3. A method of inhibiting the growth of microorganisms comprising contacting the microorganism for a sufficient time with an anti-microbial effective amount of the compound of claim 1.

4. The method of claim 3 wherein the microorganism is a bacterial organism, the amount of compound is from about 0.1 to about 5 micrograms per milliliter of medium containing the organism and the sufficient time is the entire time of growth inhibition.

5. The method of claim 3 wherein the microorganism is a bacterial organism, the amount of compound is from about 0.1 to about 50 micrograms per milliliter of medium containing the microorganism, the sufficient time is from 10 seconds to 30 minutes and the growth is inhibited by killing of the bacterial organisms.

6. The method of claim 4 wherein the bacterial organism is *A. viscosus, A. naeslundii, S. mutans, B.mel.intermed., B.mel.asacch., S.sanguis, Staphylococcus aureus* or mixtures thereof.

7. The method of claim 5 wherein the bacterial organism is *A. viscosus, A. naeslundii, S. mutans, B.mel.intermed., B.mel.asacch., S.sanguis, Staphylococcus aureus* or mixtures thereof.

8. A compound having the formula:

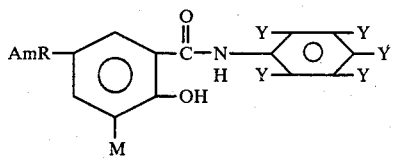

wherein R is

wherein —R'13 is a saturated or unsaturated halogenated or unhalogenated alkylene or phenylene group containing 2 through 20 carbon atoms; A is independently at each occurrence —H, —OH, -halogen, lower alkoxy, lower alkyl, —SH, thioalkyl, phenyl, phenoxy, —NH₂, lower amino and lower acyl group; m is an integer of 1 through 3; M is a radical selected from the group consisting of —C≡N, —F, —NO₂, —H, lower alkyl and lower haloalkyl and Y is independently at each occurrence —H, lower alkyl, halogenated alkyl, —NO₂, —CN, —halogen, lower acyl, —SO₂R'', or —SO₃R'' where R'' is lower alkyl or halogenated lower alkyl, provided that at least one of Y is not H or lower alkyl and the composition has a partition coefficient of at least 4, said composition being capable of inhibiting the growth of the bacterium *Actinomyces viscosis* at a concentration of less than one microgram per milliliter of a medium containing the bacterium.

9. An antiseptic somposition comprising an antimicrobial effective amount of a compound of claim 8 and a suitable carrier therefor.

10. The compound of claim 8 wherein A is —H, m=1, and at least one Y is —NO₂, —Br, —Cl, —F, or —CF₃.

11. The compound of claim 8 wherein m is 1 or 2, at least one A is not —H and Y is independently at each occurrence —H, —halogen, —NO₂, —CN, halogenated lower alkyl, —CHO, or lower acyl.

12. A compound of the formula

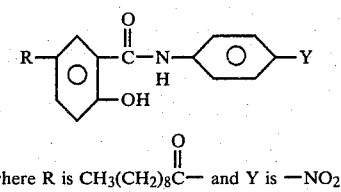

where R is CH₃(CH₂)₈C(O)— and Y is —NO₂.

13. A compound of the formula:

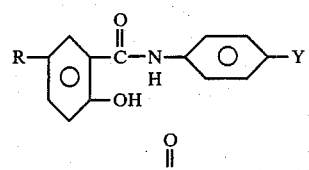

where R is CH₃(CH₂)₆C(O)— and Y is —NO₂.

14. A compound of the formula:

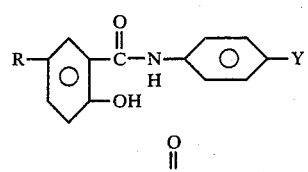

where R is CH₃(CH₂)₁₀C(O)— and Y is —NO₂.

15. A compound of the formula:

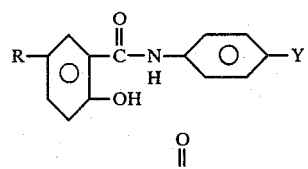

where R is CH₃(CH₂)₁₀C(O)— and Y is —Br.

16. A compound of the formula:

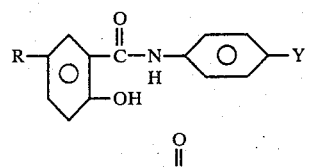

where R is CH₃(CH₂)₈C(O)— and Y is —Br.

17. A compound of the formula:

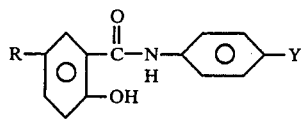

where R is CH₃(CH₂)₈$\overset{O}{\underset{\|}{C}}$— and Y is —CF₃.

18. A compound of the formula:

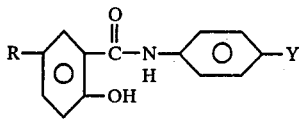

where R is CH₃(CH₂)₆$\overset{O}{\underset{\|}{C}}$— and Y is —CF₃.

19. A compound of the formula:

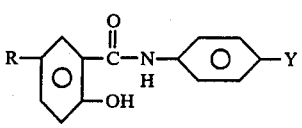

where R is CH₃(CH₂)₁₀$\overset{O}{\underset{\|}{C}}$— and Y is —CF₃.

20. A compound of the formula:

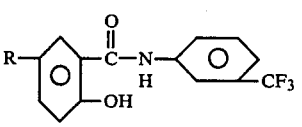

where R is CH₃(CH₂)₁₀$\overset{O}{\underset{\|}{C}}$—.

21. A compound of the formula:

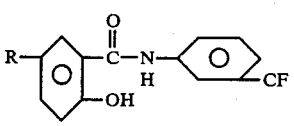

where R is CH₃(CH₂)₈$\overset{O}{\underset{\|}{C}}$—.

22. A compound of the formula:

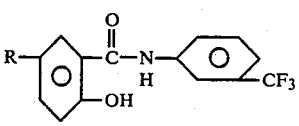

where R is CH₃(CH₂)₆$\overset{O}{\underset{\|}{C}}$—.

23. A compound of the formula:

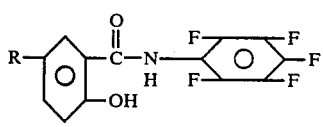

-continued where R is CH₃(CH₂)₈$\overset{O}{\underset{\|}{C}}$—.

24. A compound of the formula:

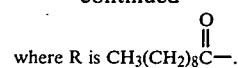

where R is CH₃(CH₂)₆$\overset{O}{\underset{\|}{C}}$—.

25. A compound of the formula:

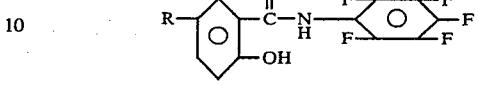

where R is CH₃(CH₂)₆$\overset{O}{\underset{\|}{C}}$—.

26. A compound of the formula:

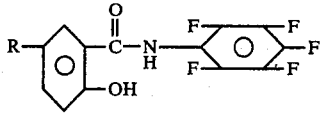

where R is CH₃(CH₂)₁₀$\overset{O}{\underset{\|}{C}}$—.

27. A compound of the formula:

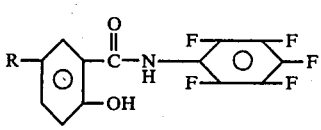

where R is CH₃(CH₂)₈$\overset{O}{\underset{\|}{C}}$— and Y is —NO₂.

28. A method for inhibiting the growth of microorganisms comprising contacting the organism for a sufficient time with an anti-microbial effective amount of the compound of claim 8.

29. The method of claim 28 wherein the microorganism is a bacterial organism, the amount of compound is from about 0.1 to about 5 micrograms per milliliter of medium containing the organism and the sufficient time is the entire time of growth inhibition.

30. The method of claim 28 wherein the microorganism is a bacterial organism, the amount of compound is from about 0.1 to about 50 microns per milliliter of medium containing the microorganism, the sufficient time is from 10 seconds to 30 minutes and the growth is inhibited by killing of the bacterial organisms.

31. Th method of claim 29 wherein the bacterial organism is *A. viscosus, A. naeslundii, S. mutans, B.mel.intermed., B.mel.asacch., S.sanguis, Staphylococcus aureus* or mixtures thereof.

32. The method of claim 30 wherein the bacterial organism is *A. viscosus, A. naeslundii, S. mutans, B.mel.intermed., B.mel.asacch., S.sanguis, Staphylococcus aureus* or mixtures thereof.

33. A method for inhibiting the growth of microorganisms comprising contacting the microorganism for a sufficient time with an anti-microbial effective amount of the compound of claim 10.

34. The method of claim 33 wherein the microorganism is a bacterial organism, the amount of compound is from about 0.1 to about 5 micrograms per milliliter of medium containing the organism and the sufficient time is the entire time of growth inhibition.

35. The method of claim 33 wherein the microorganism is a bacterial organism, the amount of compound is from about 0.1 to about 50 micrograms per milliliter of medium containing the microorganism, the sufficient time is from 10 seconds to 30 minutes and the growth is inhibited by killing of the bacterial organisms.

36. The method of claim 34 wherein the bacterial organism is *A. viscosus, A. naeslundii, S. mutans, B.mel.intermed., B.mel.asacch., S.sanguis, Staphylococcus aureus* or mixtures thereof.

37. The method of claim 35 wherein the bacterial organism is *A. viscosus, A. naeslundii, S. mutans, B.mel.intermed., B.mel.asacch., S.sanguis, Staphylococcus aureus* or mixtures thereof.

* * * * *